United States Patent [19]

Broedel et al.

[11] Patent Number: 5,569,838
[45] Date of Patent: Oct. 29, 1996

[54] PROCESS AND DEVICE FOR MEASURING A GAS MEDIUM WITH A CHEMICAL SENSOR

[75] Inventors: Axel Broedel, Lenzkirch; Thomas Springmann; Reinhold Munch, both of Freiburg; Armin Bader, Braeunlingen, all of Germany

[73] Assignee: Testo GmbH & Co., Lenzkirch, Germany

[21] Appl. No.: 398,928

[22] Filed: Mar. 6, 1995

[30] Foreign Application Priority Data

Mar. 5, 1994 [DE] Germany ............... 44 07 345.3

[51] Int. Cl.[6] .................... G01N 27/416; G01N 1/22
[52] U.S. Cl. .................... 73/23.31; 422/94; 436/137; 73/23.21
[58] Field of Search .................... 73/23.31, 23.20, 73/23.21; 422/83, 94; 436/136–138, 179

[56] References Cited

U.S. PATENT DOCUMENTS

| | | | |
|---|---|---|---|
| 3,447,359 | 6/1969 | Kapff | 73/23.2 |
| 4,134,289 | 1/1979 | Bohl et al. | 73/23.31 |
| 4,555,931 | 12/1985 | Amimoto et al. | 73/23.2 |
| 5,041,265 | 8/1991 | Koike et al. | 73/23.31 |
| 5,221,517 | 6/1993 | Takeda | 73/23.2 |
| 5,246,594 | 9/1993 | Stegemann | 210/743 |
| 5,270,009 | 12/1993 | Nakamori et al. | 73/23.31 |
| 5,272,907 | 12/1993 | Hakala | 73/23.2 |
| 5,297,432 | 3/1994 | Traina et al. | 73/23.31 |

FOREIGN PATENT DOCUMENTS

| | | |
|---|---|---|
| 285650A5 | 12/1990 | German Dem. Rep. . |
| 285652A5 | 12/1990 | German Dem. Rep. . |
| 285651A5 | 12/1990 | German Dem. Rep. . |
| 225029 | 11/1985 | Japan ............. 73/23.2 |
| 5135 | 1/1987 | Japan ............. 73/23.2 |
| 1144493 | 11/1986 | U.S.S.R. .......... 73/23.2 |
| 1446522 | 12/1988 | U.S.S.R. .......... 73/23.2 |
| WO94/16369 | 7/1994 | WIPO . |

*Primary Examiner*—Hezron E. Williams
*Assistant Examiner*—Daniel S. Larkin
*Attorney, Agent, or Firm*—R. Lewis Gable

[57] ABSTRACT

The invention relates to a process and a device for measuring a gas medium with a chemical sensor that has a nominal measuring range. The chemical sensor is exposed to a gas mixture consisting of sample gas stream and dilution gas stream. In order to ensure that the chemical sensor always works within its nominal measuring range, the dilution ratio is readjusted. According to the invention, the dilution ratio is determined by substance concentration measurement of a defined substance component.

18 Claims, 2 Drawing Sheets

PROCESS AND DEVICE FOR MEASURING A GAS MEDIUM WITH A CHEMICAL SENSOR

FIELD OF THE INVENTION

The invention relates to a process and a device for measuring a gas medium with at least one chemical sensor.

BACKGROUND OF THE INVENTION

Chemical or electrochemical sensors and, in particular, gas sensors for gaseous media, work only inadequately outside their nominal, i.e., optimal measuring range. The respective sensors can also be damaged outside this nominal measuring range, which must be prevented. On the other hand, such chemical sensors should also be usable outside their nominal measuring ranges for gas concentration measurements.

Them are several known publications dealing with the problem of staying within a nominal measuring range in detection systems with sensors. To this end, a variable dilution of the measured sample medium is suggested. Among those known is a polycyclic hydrocarbon analyzer for the real time measurement of combustion aerosols, called PAS 1000e, by Seefelder MeBtechnik GmbH & Co. Vertriebs-KG, which is used for air quality monitoring. In order to stay within the measuring range of the photoelectric sensor used in this device, the measured aerosol must be diluted. The dilution is adjusted manually via a dial switch. The dilution of the measured aerosol ensures a safe measurement in the linear range of the photoelectric sensor. [East German] Patent publications DD 285 650 A5, DD 285 651 A5 and DD 285 652 A5, in contrast, describe a dynamic ratio for diluting a measuring medium in order to stay within the measuring range of a detection system. The processes described in these three publications assume that manual adjustment of the dilution in order to stay within the measuring range is questionable. For this reason, a feedback control system is described for a process-oriented readjustment of the dilution. The feedback control system provides a dynamic readjustment of the dilution ratio by evaluating the detection signal of the sensor in such a way that the mixing concentration that can be detected by the sensor is kept within the optimum—and thus nominal—measuring range of the sensor. The actual measuring result is determined by evaluating the detection signal of the sensor while considering the dilution ratio. The measuring medium is always a fluid. The adjusted dilution ratio is determined in each case by a volumetric flow rate measurement. This is accomplished with a dilution arrangement which dilutes the measured fluid medium, e.g., in nine dilution steps, from a dilution ratio of 1:256 in a dual reduction sequence to a dilution ratio of 1:1.

The problem with this volumetric flow rate measurement is the relatively complicated equipment. For example, it is required on the one hand, (see DD 285 651 A5) that metering vessels with a fixed volume be provided, which must also have a fixed ratio relative to each other. To achieve defined mixing ratios, these metering vessels must be interconnected with processor control. The line pieces necessary between the metering vessels and the associated valves must also be taken into consideration. On the other hand (see DD 285 652 A5), the volumetric flow rate measurement also requires a pump arrangement and hoses for transporting the measured medium, as well as means for changing the flow cross-section of the hoses so that the respective fluid volume can be determined by means of the hoses according to the Hagen-Poiseuille law.

The task underlying the invention consists of describing a process and a device for measuring a gas medium with at least one chemical sensor, whose nominal measuring range is safely complied with, even in the case of gas medium concentrations outside this nominal measuring range, and that is easily realized.

SUMMARY OF THE INVENTION

The process according to the invention consists essentially of mixing a sample gas stream with a dilution gas stream in an adjustable dilution ratio, and of determining the dilution ratio using a substance concentration measurement of a defined substance component, at least after the mixing process. According to the invention, the gas mixture is fed to the chemical sensor which has a nominal measuring range for generating a detection signal. The dilution ratio is readjusted by evaluating the detection signal of the chemical sensor so that the gas mixture concentration that can be detected by the chemical sensor stays safely within the nominal measuring range of the chemical sensor. The actual measuring value for the gas medium is determined by evaluating the detection signal while considering the adjusted dilution ratio.

This process according to the invention makes it possible to detect the composition of the measured gas medium with high accuracy across a wide concentration range, and thus can be widely used, in particular in detection systems with electrochemical sensors used in industry and environmental protection.

According to the invention it is, for example, possible to continuously remove a sample gas stream by means of a sampling probe. A dilution stream with a known composition is mixed into a defined amount, determined by measuring, in the sample gas stream inside a mixing arrangement so that the dilution ratio can be adjusted or readjusted by means of the detection of the target measuring value. The dilution ratio is calculated by repeated measurement of the substance component in the gas mixture stream and is used for determining the measuring value and for readjusting. An electronic control process by means of a microprocessor is particularly suitable for this purpose.

The process according to the invention can be used for measuring gas media with complex compositions, i.e., particularly for process gas and emissions measurement.

The process according to the invention can also be used in situations where abrupt changes of the substance concentration of the measured gas medium occur, or where the magnitude of the initial value of the substance concentration in the sample gas stream is unknown; the reason for this is that, according to an advantageous further development of the invention, initially a dilution ratio is used that is so high that the chemical sensor functions safely within its nominal measuring range. In this way, an overloading or damaging of the chemical sensor and a reduction in the quality of the measuring result is thus effectively-prevented according to the invention.

According to a further development of the invention, the defined substance component, which may, for example, be oxygen, is present in the dilution gas stream in a known and constant amount. The substance concentration measurement of this substance component is then performed both in the sample gas stream and in the gas mixture stream. Only two sensors are thus required, e.g., oxygen sensors, for detecting the oxygen component in the sample gas stream and in the gas mixture stream.

If, according to a further variation of the invention, the defined substance component is not present in the sample gas stream, and if the defined substance component is present in the dilution gas stream in a known and constant amount, the substance concentration measurement according to the invention may be performed by determining the substance component exclusively in the gas mixture stream. This results in a particularly simple construction of a device for performing the process, since in addition to the chemical sensor only one other sensor must be provided.

It was found that the use of an air stream is advantageous as a dilution gas stream, since then no other containers must be provided for a dilution medium. Since air is after all present everywhere, it is sufficient that the air is passed over an air filter that may possibly be required, and that this air stream is mixed as a dilution gas stream with the sample gas stream. If, for instance, oxygen is not present as a substance component in the sample gas stream, then the dilution ratio of sample gas stream and dilution gas stream can be easily determined by detection of the oxygen content in the gas mixture. If the substance component, here oxygen, is not present in the sample gas stream, it is naturally not necessary to perform a detection of this substance component on the sample gas side.

A further development according to the invention provides that several chemical sensors are furnished for the detection of several substance values of the gas medium, and that a regulation of the dilution ratio is performed in accordance with a detection signal of that chemical sensor, from whose nominal measuring range the greatest deviation is expected at the beginning of the process. This ensures that the chemical sensor subjected to the greatest risk is safely protected.

According to a further development of the invention, a value of the dilution ratio that must be readjusted is determined and set during the readjusting of the dilution ratio from an increasing measuring value progression or a previous measuring value. In addition, a defined measuring value optimum can also be determined by step-by-step comparison with the detection signals of the chemical sensor.

Finally, it is possible that based on the detection signal of the chemical sensor or a previous measurement, the expected detection signal of the following measurement is determined, and then the dilution ratio can be set by forming a gradient. This accomplishes a prediction of the next detection signal and thus results in a faster readjustment of the measuring value. This is an advantage in particular for sensitive detection systems.

It was found useful that the dilution ratio is regulated by controlling the pump output of one or more pumps which transport the sample dilution and/or gas mixture.

The regulation of the dilution ratio can however also be controlled, e.g., via one or more control valves and/or mass flow controllers or via magnetic valves and capillaries having identical or different aperture cross-sections, so that the dilution gas stream is metered to the sample gas stream and vice versa.

According to the invention, the detection signal of the chemical sensor or of the chemical sensors can be kept within a predetermined interval of the nominal measuring range by either incremental or continuous change in the dilution ratio. A step-by-step dilution of the dilution ratio may be provided, e.g., in nine dilution steps, starting with a dilution ratio of 1:256 in dual reduction sequence to a dilution ratio of 1:1.

When chemical sensors are used it is also advantageous that a linear increase or decrease of the dilution ratio is provided. Typical substance concentration measuring ranges for chemical and electrochemical sensors range from 0 to 1 Vol. % (0 to 10,000 ppm). There are also sensors for higher measuring ranges. The dilution is also reasonable for these, so that concentrations up to 100% can be measured.

The invented process of the dynamic dilution of gaseous media for the purpose of staying within the measuring range of chemical sensors thus utilizes the mixing of a dilution stream with a defined and preferably constant composition with the sample gas stream. By using the electric detection signal of the chemical sensor, it is determined whether the nominal measuring range of the chemical sensor is complied with or not. If the detection signal is outside this nominal measuring range or outside a defined partial measuring range inside this measuring range, then the dilution ratio of sample gas stream and dilution gas stream is adjusted. The dilution ratio is determined here by means of substance component measurement in the sample dilution and/or gas mixture stream.

An invented device for performing the measurement of a gas medium with at least one chemical sensor is provided with the following elements:

a) a device for removing the sample gas stream, b) a device for supplying a dilution gas stream, c) a mixing arrangement for mixing the dilution gas stream and the sample gas stream into one gas mixture in accordance with an adjustable dilution ratio, d) a chemical sensor for detecting a gas mixture concentration of the gas mixture, and e) a control device, preferably a microprocessor, for readjusting the dilution ratio in accordance with the concentration of a substance contained in the gas mixture in such a way that the gas mixture concentration that can be detected by the chemical sensor is kept within the nominal measuring range of the chemical sensor.

Another sensor for detecting the defined substance may be arranged in the gas mixture stream and/or the sample gas stream, depending on whether the defined substance is present in the sample gas stream or not.

BRIEF DESCRIPTION OF DRAWINGS

The invention and its advantages are explained in the form of examples in more detail below with reference to two figures.

In the following FIGS. 1 and 2, identical reference numbers are used for the same parts having the same significance, unless stated otherwise.

DESCRIPTION OF A PREFERRED EMBODIMENT

Figure 1:
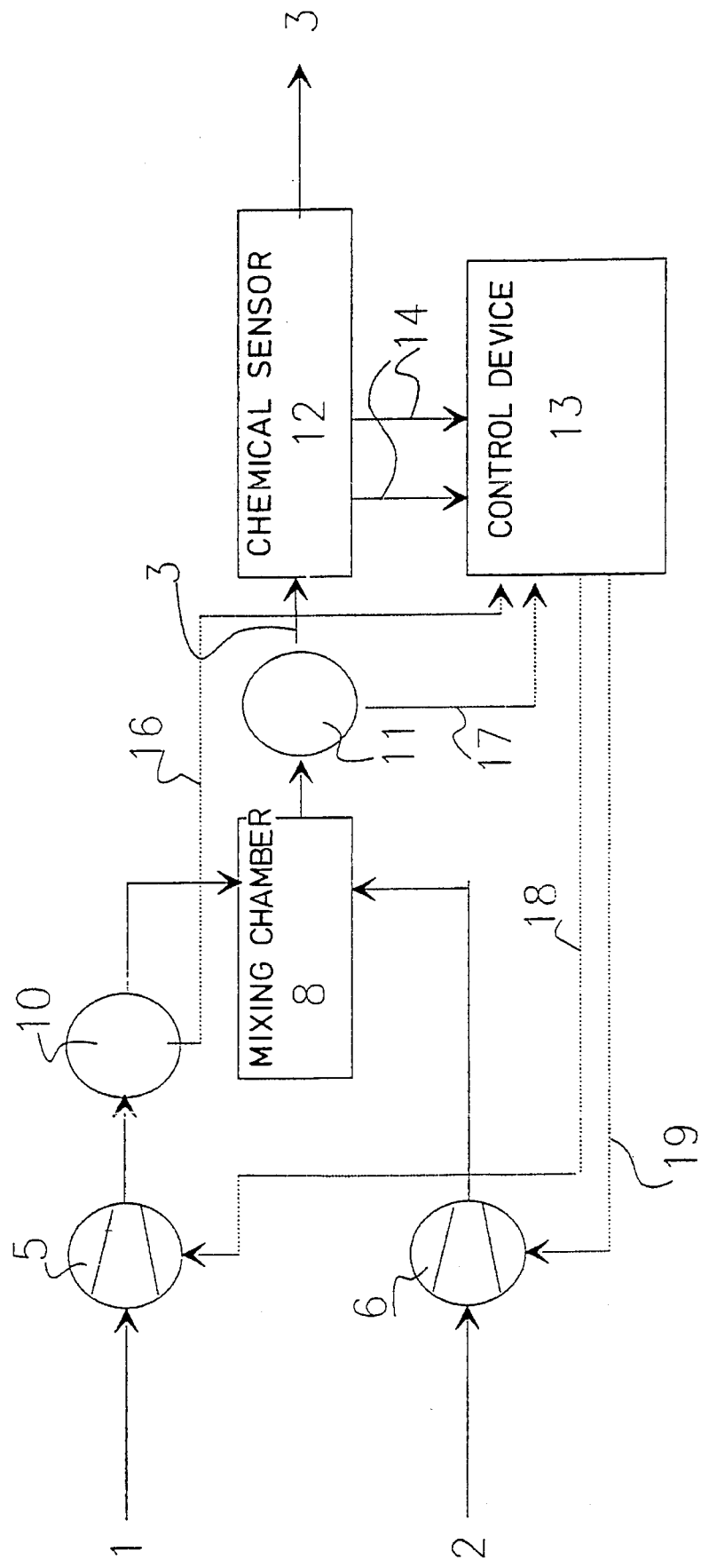
FIG. 1 shows a principal switching diagram for performing the process according to the invention.

FIG. 1 shows a sample gas stream with the reference number 1 and a dilution gas stream with the reference number 2. The sample gas stream is fed via a pump 5 to a mixing arrangement or chamber 8, while the dilution gas stream 2 is fed via a pump 6 to the mixing arrangement 8.

A sensor 10 is arranged in the supply line from the pump 5 to the mixing arrangement 8. The discharge of the mixing arrangement 8 is connected to a detection device, in which at least one chemical sensor 12 is arranged. A gas mixture stream 3 consisting of the sample gas stream 1 and the dilution gas stream 2 in a defined dilution ratio is fed to this chemical sensor 12. The supply line from the mixing arrangement 8 to the chemical sensor 12 holds another sensor 11.

There is also a control device 13 that receives one or more detection signals 14 from the chemical sensor 12, and additional sensor signals 16, 17 from the other sensors 10, 11. Depending on these detection signals 14 and sensor signals 16, 17, the control device 13 controls the pump output of pumps 5 and 6 via adjusting signals 18, 19.

The control device 13 that controls the pump output of pumps 5 and 6 is used to specifically adjust the dilution of the sample gas stream 1, thus ensuring compliance with the nominal measuring range or optimal partial measuring range of the chemical sensor 12. Obtaining a correct measuring value requires that the dilution ratio is exactly known in order that the detection signal is corrected in accordance with this dilution ratio, so that finally the real concentration value of the gas mixture is determined.

The dilution ratio is determined according to the invention by a substance concentration measurement. The example in FIG. 1 assumes that the substance component is present in the dilution gas stream 2 in a known ratio, and is also present in the sample gas stream 1. According to the invention, it is therefore only necessary to provide a sensor 10 in the supply line from pump 5 to the mixing arrangement 8, and another sensor 11 in the supply line from the mixing arrangement 8 to the chemical sensor 12, while such a sensor need not be provided in the supply line of the dilution gas stream 2 to the mixing arrangement 8.

If X is the substance value to be determined by way of the dilution ratio, the dilution factor is obtained according to the following formula:

$$\text{Dilution factor} = \frac{X2 - X1}{X2 - X3},$$

whereby the numbers 1, 2, and 3 again represent respectively the sample gas stream, the dilution gas stream, and the gas mixture stream. If air is used as a diluting medium and the defined substance component is oxygen then X2 would be 21 Vol. %. The real concentration value is thus derived from the product of the sensor measuring value of the chemical sensor 12 and the dilution factor.

In the embodiment of FIG. 1, it is assumed that the substance component is present in the dilution gas stream in a known and constant amount. The defined substance component may, for example, be oxygen. If the component oxygen is not present in the sample gas stream 1, then it would not even be necessary to provide the additional sensor 10 in the arrangement of FIG. 1. The dilution ratio is then obtained exclusively from the oxygen content value detected by the additional sensor 11.

The invented process for the dynamic regulation of the dilution of the investigated sample gas stream 1, while staying within the working range of the chemical sensor 12, can be performed by following these steps:

1. Definition of a maximum possible concentration of the chemical sensor 12 and, derived from this, the presetting of the maximum dilution ratio.
2. Calculation of the new dilution ratio in the control device 13 from the measuring value of the chemical sensor 12 or an increasing behavior of the measuring value that is determined by the chemical sensor 12 based on the inertia of the detection system, and dynamic readjustment via the control device 13 in connection with adjusting equipment, such as pumps 5, 6, magnetic and/or control valves, mass flow controllers, etc.
3. Determination of the currently set mixing or dilution ratio by means of substance concentration measurement by computing this value together with the current sensor concentration of the chemical sensor 12, in order to determine the real substance concentration present in the sample gas stream 1.
4. Dynamic readjustment of the dilution ratio via the sensor concentration in the case of a fluctuating concentration composition of the sample gas stream 1, in such a way that the sensor concentration of the chemical sensor 12 is maintained within a partial measuring range at approximately a defined, set value, in particular by an incremental, interval-like or continuous change of the dilution ratio.
5. If a multicomponent system is provided, i.e., a detection system with a number of different chemical sensors 12, the remaining component can be measured in the respective optimum partial measuring range through repeated dynamic readjustment of the dilution ratio by gradual or optional removal of the respective chemical sensor 12 with the highest load.

Such a procedure makes it possible to use the chemical sensor 12 for measuring concentrations outside the nominal measuring range of this chemical sensor 12, and to dynamically readjust the dilution in such a way when the sample gas stream 1 changes that the measuring values of the chemical sensor 12 still remain within the permissible measuring range and there is no risk to the chemical sensor 12.

Figure 2:
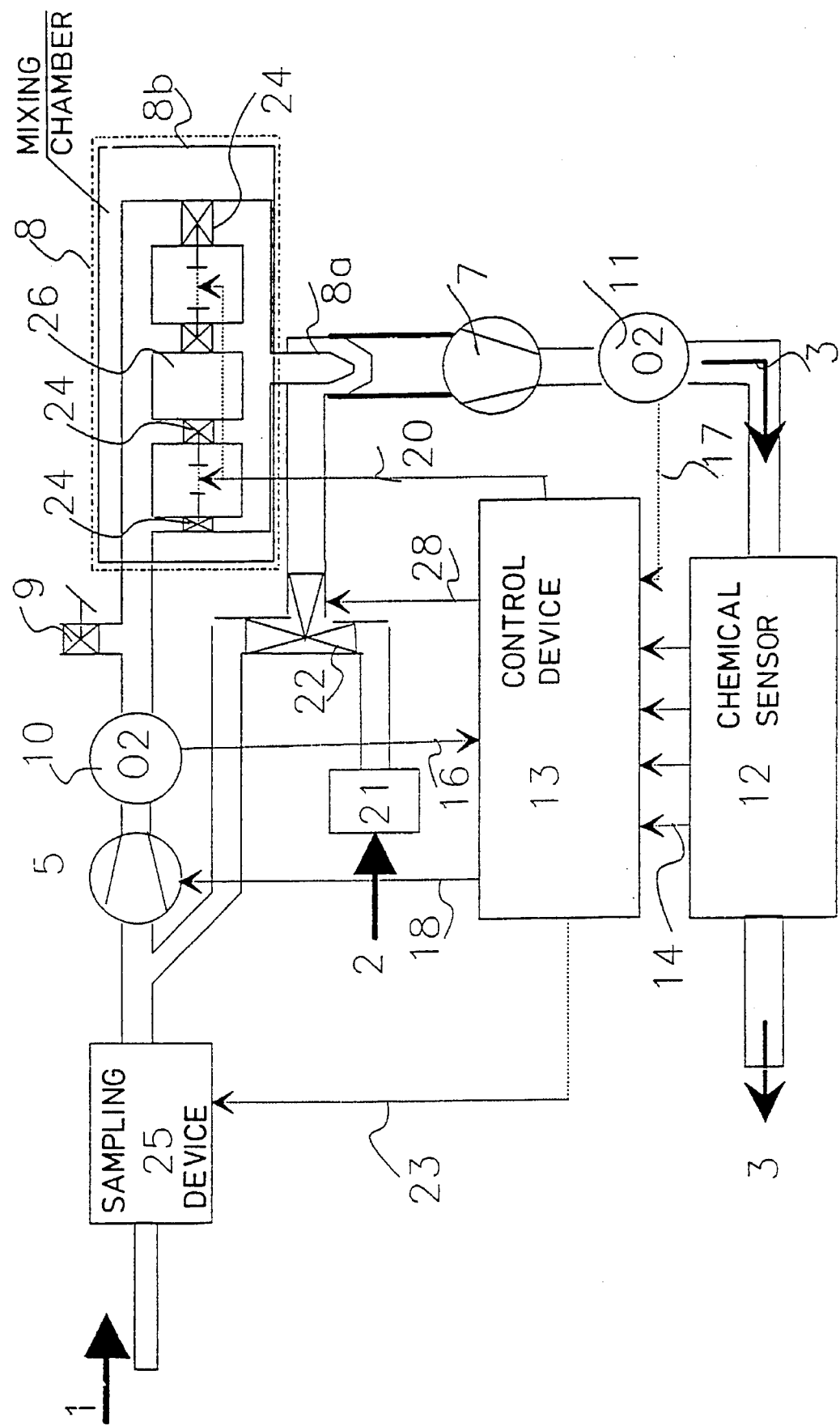
FIG. 2 shows a detailed portrayal of the process according to the invention, using the example of a detection system with electrochemical gas sensors and oxygen sensors for determining the dilution ratio.

FIG. 2 shows a detailed switching diagram using the example of a detector system with electrochemical gas sensors. The sample gas stream 1 is transported via a preparation device 25, where the sample gas stream 1 is removed from the gas stream to be measured and is prepared in a suitable manner, via pump 5 to the mixing arrangement 8. The sensor 10 in the line supplying the sample gas stream 1 to the mixing arrangement 8 is used to detect the oxygen content, i.e., the 02 content. This causes the sample gas stream 1 to be analyzed for its oxygen content. An overpressure, which is preferably constant, is realized in the mixing arrangement 8 on the pressure side by way of an overpressure discharge valve 9 in the supply line to the mixing arrangement 8.

The dilution gas stream 2, in this case again an air stream, is passed via a filter 21, here an air filter, and a valve 22 that is constructed as a three-way valve to the mixing arrangement 8.

The mixing arrangement 8 has a metering device 8b and a mixing chamber 8a. The metering device 8b is provided with capillaries 24, that preferably have different diameters, and with valves 26. The control device 13 controls the valves 26 that connect with the capillaries 24 in such a way that a defined amount of the sample gas stream 1 reaches the mixing chamber 8a. The dilution gas stream 2 in the form of the air gas stream is added to the defined amount of sample gas stream 1 in this mixing chamber 8a. The air gas stream is passed through valve 22.

The valves 26 of the metering device 8b are preferably magnetic valves whose openings define different dilution ratios which are roughly predefined by an adaptation between the capillary aperture cross-sections and the pump output of the pump 7 that is arranged behind the mixing chamber 8a. The pump 7, via the filter 21 and the valve 22, sucks in an air stream, to which the sample gas stream 1 is measured and added in the mixing chamber 8a.

On the discharge side, the pump 7 is connected to a detection system with at least one chemical sensor 12 in the form of an electrochemical gas sensor. In this way the gas mixture stream 3 composed of the sample gas stream 1 and the air gas stream 2 in a defined dilution ratio is fed to the chemical sensor 12. In addition, another sensor 11, here another $O_2$ sensor for detecting the oxygen concentration in the gas mixture stream 3, is arranged in the gas mixture stream 3. This additional sensor 11 makes it possible, together with the measuring signal of the sensor 10, which is also an $O_2$ sensor, to determine the dilution ratio in accordance with the above formula.

The dilution ratio is calculated in the control device 13. The chemical sensor 12, of which at least one is arranged in the detection system, analyzes the gas mixture stream 3 and transmits the measuring result in the form of one or more detection signals 14 to the control device 13. The control device 13 also receives further input signals in the form of sensor signals 16 and 17 from the additional sensors 10 and 11. By means of adjusting signals 18 and, 20, and control signals 23 and 28, the control device 13 controls the pump output of the pump 5, the valves inside metering device 8b for readjusting the dilution ratio, the preparation device 25, as well as valve 22.

If the detection system contains several chemical sensors 12 for detecting several substance values of the gas mixture stream 3, the dilution ratio is preferably regulated in accordance with a detection signal 14 of the specific chemical sensor 12, of which the greatest deviation is initially expected with respect to its nominal measuring range. This ensures the protection of this chemical sensor 12 that is at the greatest risk.

At the beginning of the measuring process, the dilution ratio is set so that the chemical sensor(s) 12 in the detection system function(s) safely within their nominal measuring range. It was found to be advantageous that the maximum possible dilution is initially set here.

To achieve a quick, either incremental or continuous, readjustment of the dilution ratio, a determination, based on the detection signal 14 of the chemical sensor 12 of a previous measurement, is made in advance in the control device 13 of the expected detection signal 14 of the following measurement, and based on this, the dilution ratio is set by means of gradient formation.

What is claimed is:

1. A process for sampling and introducing a sample of an unknown gaseous medium to a chemical sensor, the gaseous medium potentially comprising a particular gaseous substance, the chemical sensor responsive to the presence of the particular gaseous substance to provide a first electrical signal indicative of its concentration within the sample and having a nominal measuring range, said process comprising the following steps:

a) taking a sample of said unknown gaseous medium;
   b) taking and mixing a dilution gas with the sample of the unknown gaseous medium to obtain a mixture thereof in accordance with an adjustable dilution ratio, said dilution gas comprising at least one known substance component of a predetermined concentration of said dilution gas;
   c) measuring the concentration of said one known substance within said mixture to provide a second electrical signal indicative thereof;
   d) introducing said mixture to the chemical sensor and operating said sensor to provide the first electrical signal;
   e) adjusting in accordance with said second electrical signal said dilution ratio;
   f) readjusting in accordance with said first electrical signal said dilution ratio to maintain the operation of the chemical sensor within its nominal measuring range; and
   g) evaluating said first and second electrical signals to provide a measure of the concentration of the particular gaseous substance in a manner to compensate for the adjustable dilution ratio.

2. Process as defined in claim 1, characterized in that said substance component is present in said dilution gas in a known and constant amount, and that a substance concentration measurement of said substance component is also performed in said sample of said unknown gaseous medium.

3. Process as defined in claim 1, characterized in that said substance component is not present in said sample of said gaseous medium and is present in said dilution gas in a known and constant amount, and that a substance concentration of said substance component is measured only in said gas mixture.

4. Process as defined in claim 1, characterized in that said substance component is oxygen.

5. Process as defined in claim 1, characterized in that an air stream is used as said dilution gas.

6. Process as defined in claim 1, characterized in that at the beginning of said process the dilution ratio is set at such a value that the chemical sensor functions safely within its nominal measuring range.

7. Process as defined in claim 1, characterized in that several chemical sensors are provided for the detection of several substance values of the gas medium, and that a regulation of said dilution ratio is performed in accordance with said first electrical signal of that chemical sensor of which the greatest deviation is initially expected in respect to its nominal measuring range.

8. Process as defined in claim 1, characterized in that during the readjustment of said dilution ratio, a value of the dilution ratio that must be set anew is determined from an increasing measuring value progression or a previous measuring value and is set.

9. Process as defined in claim 1, characterized in that, based on said first electrical signal of the chemical sensor of a previous measurement, the expected said first electrical signal of the following measurement is determined, and based on this, said dilution ratio is set by means of gradient formation.

10. Process as defined claim 1, characterized in that said first electrical signal of the chemical sensor is maintained by means of incremental or continuous changes of the dilution ratio within a predetermined interval of the nominal measuring range.

11. Apparatus for taking a sample of an unknown gaseous medium potentially with a particular gaseous substance and providing a measure of the concentration of the particular gaseous substance, said apparatus comprising:

a) a mixing chamber;
   b) means for taking a sample of the unknown gaseous medium into said mixing chamber;
   c) means for introducing a dilution gas along with said sample of the unknown gaseous medium into said mixing chamber to provide a mixture thereof in accordance with an adjustable dilution ratio within said mixing chamber, said dilution gas having at least one known substance component of a predetermined concentration of said dilution gas;

d) a chemical sensor coupled with said mixing chamber to receive therefrom said mixture and to provide a first electrical signal indicative of the concentration within said mixture of the particular gaseous substance, said chemical sensor having a nominal measuring range;

e) at least one further sensor to provide a second electrical signal indicative of the concentration of the one known substance component; and f) control means responsive to said first and second electrical signals for operating said introducing means whereby said dilution ratio is adjusted in such a manner that said chemical sensor operates within said nominal measuring range.

12. Apparatus as defined in claim 11, characterized in that said one further sensor for detecting the known substance component is coupled with said mixing chambers to sense the gas mixture.

13. Apparatus as defined in claim 11, characterized in that said one further sensor for detecting said known substance component is coupled with the sample gas.

14. Apparatus as defined in claim 12, characterized in that said one further sensor for detecting said known substance component is an oxygen sensor.

15. Apparatus as defined in claim 11, characterized in that air is provided as said dilution gas.

16. Apparatus as defined in claim 11, characterized in that said mixing chamber is provided with a defined number of capillaries that have different diameters, each having a valve associated with it.

17. Apparatus as defined in claim 11, characterized in that an overpressure can be set in a supply line supplying said sample of said unknown gas to said mixing chamber.

18. Apparatus as defined in claim 17, characterized in that an overpressure discharge valve is arranged in a supply line that conducts said sample of said unknown gaseous medium to said mixing chamber.

* * * * *